United States Patent [19]

Hansson et al.

[11] Patent Number: 5,894,070
[45] Date of Patent: Apr. 13, 1999

[54] HARD TISSUE STIMULATING AGENT

[75] Inventors: Hans-Arne Hansson, Hovås; Gunilla Johansson-Rudén, Askim; Olle Larm, Bromma, all of Sweden

[73] Assignee: Astra Aktiebolag, Sodertalje, Sweden

[21] Appl. No.: 08/505,353

[22] PCT Filed: Jul. 13, 1995

[86] PCT No.: PCT/SE95/00857

§ 371 Date: Aug. 30, 1995

§ 102(e) Date: Aug. 30, 1995

[87] PCT Pub. No.: WO96/02259

PCT Pub. Date: Feb. 1, 1996

[30] Foreign Application Priority Data

Jul. 19, 1994 [SE] Sweden ................ 9402528

[51] Int. Cl.$^6$ .............. A61K 31/715; A61K 31/73; A61K 31/725; A61F 2/02
[52] U.S. Cl. .............. 514/55; 514/54; 514/56; 514/59; 623/11; 623/16
[58] Field of Search .............. 514/54, 55, 56, 514/59; 623/11, 16

[56] References Cited

U.S. PATENT DOCUMENTS 4,613,655  9/1986  Larm ........................ 536/20
5,470,911  11/1995  Rhee et al. .................. 525/54.1

FOREIGN PATENT DOCUMENTS 9602259  7/1995  WIPO.

OTHER PUBLICATIONS

Muzzarelli et al. *Biomaterials* 1993, 14(12), 925–929.
Hammar et al. *Chitin Chitosan, Proceeding Int. Conf.*, 2nd 1982, 213–215.
Kawakami et al. *Biomaterials* 1992, 13, 759–763.
Borah et al. In "Advances in Chitin and Chitosan", Brine et al., eds., Elsevier (Netherlands) 1992, 47–53.
R.A.A. Muzzarelli et al. Osteoconductive properties of methylpyorolidinone chitosan . . . *Biomaterials* 14:928 (1993).
L.P. Nilsson "Effects of Hyperbaric Oxygen . . . " *Swedish dental journal*/Suppl. 64: 19–25 (1989).

*Primary Examiner*—Kathleen K. Fonda
*Attorney, Agent, or Firm*—White & Case LLP

[57] ABSTRACT

The use of chitosan and a polysaccharide immobilized thereto selected from heparin, heparan sulphate, chondroitinsulphates and dextran sulphate for the manufacture of an agent capable of providing stimulated regeneration of hard tissue;

a process for stimulating regeneration of hard tissue in connection with so called osseointegration; and implant intended for integration into hard tissue, particularly bone tissue.

17 Claims, No Drawings

HARD TISSUE STIMULATING AGENT

This application is the U.S. National Stage entry under 35 U.S.C. 371 of PCT/SE95/00857, filed Jul. 13, 1995.

TECHNICAL AREA

The present invention relates to new techniques for stimulating or accelerating regeneration of hard tissue in connection with so called osseointegration, for example the effect sought in the implantation of foreign implants in hard tissue, particularly bone tissue. The invention also relates to a process for carrying out such osseointegration while applying the new techniques according to the invention. Furthermore, the invention relates to the generation of new bone in relation to bone tissue defects or otherwise need of bone tissue.

BACKGROUND OF THE INVENTION

Implants intended for anchorage in hard tissue, particularly bone tissue, have enjoyed an ever increasing use in odontology, orthopedics, neurosurgery, hand surgery and plastic and reconstructive surgery. Long term anchorage of implants in bone has been achieved with titanium, and it can be assumed that titanium-based materials also in the future will be used to a large extent as the material of choice for implants and prosthesis.

A clinical problem when dealing with so called osseointegration is the fact that the implant cannot be subjected to a load before sufficient bone anhorage has been achieved, which may require as much as 6 to 9 months. It is therefore clinically of utmost importance to accelerate the healing process by providing stimulated bone formation in association with the implants. There is also a need to regenerate bone in order to bridge defects or sections where bone resorption has taken place in for example toothless parts of jaws or where bone tissue has been lost due to e.g. trauma, tumor or surgery.

SUMMARY OF THE INVENTION

The main object of the present invention is to stimulate growth of cells in hard tissue, for example bone cells, so that the hard tissue volume will increase.

Another object of the invention is to provide means resulting in the formation of regenerated bone tissue of dominantly lamellar, compact type, whereas the extent of formation of scar tissue will be minimized.

Yet an object of the invention is to provide a new agent capable of providing in connection with implants in hard tissue stimulated regeneration of hard tissue, for example bone tissue.

Another object of the invention is to provide a process for improved osseointegration in connection with implantation of foreign implants in hard tissue while stimulating regeneration of tissue.

Another object of the invention is to provide implants treated with an agent stimulating regeneration of hard tissue.

For these and other objects which will be clear from the following disclosure there is provided through the invention a new use of chitosan and a polysaccharide immobilized thereto selected from heparin, heparan sulphate, chondroitin-sulphates and dextran sulphate. This new use relates to the manufacture of an agent capable of providing stimulated regeneration of hard tissue. Such stimulated regeneration may for example be provided in connection with implants in hard tissue, such as bone tissue.

The polysaccharide can be immobilized to the chitosan matrix in several ways, for example by ionic bonds, by covalent binding either multipoint or endpoint binding, or by mechanical fixation in the chitosan matrix in connection with precipitation of the chitosan from solution. Ionic bonds and covalent bonds are preferred immobilization forms.

The hard tissue stimulating agent according to the invention may be present in different physical forms, for example as a membrane, a powder, a gel, beads or a solution. In the case where an implant is intended, that part of the implant which is to be integrated in hard tissue can be dipped for application of the agent onto the implant. The agent can, of course, also be supplied to the hard tissue per se, for example in a cavity provided in bone tissue.

The material preferred for the implantation is titanium but other implant materials may as well be used.

Chitosan is a linear 1,4-bound polysaccharide built up from $\beta$-D-glucose amine units. The chitosan is manufactured by N-deacetylation of chitin, a polymer forming the shell of inter alia insects and shellfish. Commercially, chitin is recovered from crab and shrimp shells which constitute waste products from the fishing industry. By controlling the alkali treatment of chitins, chitosans of varying degree of N-acetylation can be produced. When treating chitin with concentrated alkali, usually sodium hydroxide, N-deacetylation thus takes place, i.e. acetamido groups are converted into amino groups to form chitosan.

The physical properties of chitosan affecting its usefulness depend on the degree of N-acetylation, the molecular weight and the homogeneity. Chitosan is biodegradable, both by chitinase in the digestive system and by lysozyme and other enzymes in the body.

It is preferred in connection with the use of the present invention that the chitosan has a degree of N-acetylation of at most about 90% and preferably at most about 50%. It is particularly preferred that the degree of N-acetylation is less than about 25%.

The preferred polysaccharide for immobilization to the chitosan matrix is heparin or heparan sulphate. A special technique for covalent coupling of heparin to matrices containing amino groups is described in U.S. Pat. No. 4,613,665.

The invention also provides for a process for stimulating and/or accelerating regeneration of hard tissue, for example in connection with so called osseointegration. This process is characterized in that before the implantation there is applied to the implant and/or the hard tissue a quantity suitable for stimulation of the defined agent prepared starting from chitosan and a polysaccharide immobilized thereto selected from heparin, heparan sulphate, chondroitin-sulphates and dextran sulphate. Osseointegration is the optimal form for long term anchorage of an implant of of non-autologous and various foreign materials into hard tissue, particularly bone tissue.

In connection with carrying out this process the agent may be applied in the form of a powder, a solution, a gel, beads, a film or a membrane. Alternatively, the agent may be applied by dipping that part of the implant intended to be integrated into hard tissue in a solution of the appropriate constituents chitosan and a polysaccharide immobilized thereto.

The invention also includes implants intended for integration in a hard tissue, particularly bone tissue. In such implants the part of the implant to be integrated is coated with an agent stimulating regeneration of hard tissue comprising chitosan and a polysaccharide immobilized to the chitosan and selected from heparin, heparan sulphate, chondroitinsulphates and dextran sulphate. It is particularly preferred that the implant comprises titanium.

EXAMPLES OF PREFERRED EMBODIMENTS

The present invention will in the following be illustrated by non-limiting examples. In these percentages and parts refer to weight if not otherwise stated.

Example 1

Coating of a titanium screw with chitosan

Titanium screws are immersed into a 2% acetic acid solution of chitosan (1% w/v) and are allowed to remain in said solution for 15 min. The chitosan is Sea Cure 313, Pronova Biopolymer, 15% N-acetylation). The treated titanium screws are then dried in a heat cabinet for 16 h at 70° C. and then neutralized in 1 M NaOH and repeatedly rinsed with distilled water and again dried in a heat cabinet. The screws are packed in a package of the type "peel open" and sterilized with ethylene oxide.

Example 2

Titanium screws with ionically bonded heparin

Screws coated with chitosan according to Example 1 are transferred into a solution consisting of 125 mg heparin (Pig Mucosa, Kabivitrum ) in 500 mL of distilled water where they are allowed to remain for about 16 h, after which they are rinsed in distilled water and dried at room temperature. The screws are packed in a package of the type "peel open" and sterilized with ethylene oxide. The amount of immobilized heparin is about 2 µg/cm$^2$.

Example 3

Titanium screws with covalently bonded heparin (End-point attachment)

Heparin is dissolved in water (300 mL). The solution is cooled to 0° C. in ice water and maintained cold. First, there is added sodium nitrite (NaNO$_3$, 10 mg) and then acetic acid (2 mL) to the solution under stirring. The reaction mixture is maintained at 0° C. for 2 h, dialyzed and freeze dried. The yield is 0.7 g.

Titanium screws coated with chitosan in accordance with Example 1 are transferred into a solution containing 125 mg of the above nitrite-degraded heparin, 15 mg NaCNBH$_3$, in 500 mL distilled water and pH is adjusted to 3.9 with 0.1 M Hcl. The reaction mixture is maintained for about 16 h at room temperature. The screws are then rinsed in distilled water and dried at room temperature. The treated titanium screws are packed in a package of the type "peel open" and sterilized with ethylene oxide. The amount of immobilized heparin is about 1.5 µg/cm$^2$.

Example 4

Titanium screws with covalently bonded heparin (multi-point attachment)

A solution of sodiumperiodate-oxidized sodiumheparin is prepared in the following manner: One gram of sodiumperiodate NaIO$_4$ is dissolved in 200 mL of distilled water. Ten grams of sodiumheparin is added to the solution and the solution is stirred over night in the dark. The resulting solution, after adding 10 mL of glycerol and stirring for two hours, is dialyzed against water. The water is exchanged every other hour. This results in a solution containing periodate-oxidized heparin in a concentration of about 19 mg/mL.

Titanium screws coated with chitosan in accordence with Example 1 are transferred to a solution containing 125 mg of the above periodate-oxidized heparin, 15 mg NaCNBH$_3$ in 500 mL distilled water. The reaction is then performed exactly as described in Example 3.

Example 5

Manufacture of chitosan film 5 g hydrochloride salt of chitosan (50% degree of acetylation, Pronova) are dissolved in distilled water (0.5 L, 1% v/w). 10 mL of the solution obtained are transferred to a Petri dish and a film of chitosan is formed by evaporation and drying in a heat cabinet at 70° C. for 24 h. The film obtained is then neutralized by the addition of a sodium phosphate buffer, 0.2 M, pH 9.0. The film is left in the Petri dish in this buffer at room temperature for 2–4 h, is then washed 3–4 times with water and allowed to dry.

Example 6

Films with covalently bonded heparin (end-point attachment)

To a neutralized chitosan film prepared in accordance with Example 1 there are added 20 mL of a solution containing 125 mg nitrite degraded heparin, prepared as in Example 3, dissolved in 0.5 L water and containing 4.4 g NaCl. To the solution is added 15 mg sodium cyanoborohydride. The pH of the solution is adjusted to 3.9 using 0.5 M hydrochloric acid or another acid. The solution containing the chitosan film is allowed to stand at room temperature for 14 h, and the treated film is then washed 3–4 times with water and is allowed to dry.

Example 7

Films with ionically bonded heparin

To a neutralized chitosan film manufactured in accordance with Example 1 there is added 20 mL of a solution containing 125 mg heparin dissolved in 0.5 L water containing 4.4 g NaCl. The solution containing the chitosan film is allowed to stand at room temperature for 14 h, and the treated film is then washed 3–4 times with water and allowed to dry. The produced film can be ground to a powder for use in osseointegration in accordance with the invention.

Example 8

Biological test

As test animals there are used adult rabbits which are anaesthesized and prepared for the operation under sterile conditions, hair being removed in the knee region of the rabbit.

A distal skin section is made in the knee joint having a length of 35–40 mm against the tibias proximal part of the epiphys cartilage region. Periost is transected and under cooling by means of a continuously supplied sterile buffered saline solution there is drilled at a low rotation speed a hole through compact leg up to the marrow cavity using a 3.5 mm drill. Then there is proximally threaded an at 4 mm long titanium screw having a hexagonal head and at 6 mm distally another titanium screw, both having a diameter of 3.5 mm. Facia and skin wound are sutured using single sutures. In the experiments there are used in addition to titanium screws treated according to the Examples 1–3 also untreated titanium screws.

After 4 and 12 weeks, respectively, the rabbits are again anaesthesized. Hair is cut away in the knee region and skin incision is carried out distally of the knee joint towards tibia. The screws are dissected and identified, and the dethreading moment for the proximal screws is determined. The distal screws are prepared for light microscopy with the implant remaining in the bone in situ.

Example 9

Titanium powder with or without heparin coating

The coating of titanium powder with chitosan is performed essentially as described i Example 1 and the immobilisation is performed as described in Example 3.

The fibula on either hind leg is exposed and its muscle tissue detached along an about 10 mm long distance on the mid shaft. A 6 mm long segment of the exposed fibula is removed, both the bone and its periostium, and the defect between the bone ends is filled with titanium powder. A membrane filter made of PTFE is wrapped around to bridge the defect and to prevent granulation tissue to invade the area. On one side titanium powder coated with heparin is positioned and on the other side non-coated titanium powder. The wounds are thereafter closed. The rats are allowed to move unrestricted during 3 weeks prior to a second examination and sacrifice. Examination of the defects in the fibula on either side reveals that bone, cancellous and lamellar, is demonstrated to bridge both defects. However, the most extensive bone formation is formed at and along the heparinized titanium powder. Additionally, more lamellar i.e. well organized bone, is detected among the heparinized titanium powder.

Thus titanium powder coated with heparin as described above, stimulates new formation of bone even in the absence of periosteum.

Example 10

Osteogenic activity of ionically heparinized chitosan membrane as assessed by the fibula gap bridging technique The fibula on either hind leg is exposed on anaesthetized rats and its muscle tissue detached along an about 10 mm long distance on the mid shaft. A 6 mm long segment of the exposed fibula is removed, both the bone and its periostium, and the defect between the bone ends is wrapped with a chitosan film.

On the left side a chitosan membrane prepared as in Example 5, is positioned (chitosan with 15% acetylation) and on the right fibula defect a heparinized chitosan membrane prepared as in Example 7 (chitosan with 15% acetylation) is positioned.

To avoid that the tube, created by the membranes and bridging the 6 mm gap between the bone ends, collapses, small bone framents are positioned along the gap.

At examination after three weeks a more prominent formation of bone matrix and of bone could be demonstrated in both animals on the right side, i.e. the one with the heparinized chitosan film.

Example 11

Osteogenic activity of heparinized chitosan membrane as assessed by bone formation in a hole in the calvarium It is well established that if defects exceeding certain dimensions are created in bone, such defects are healed by the formation of a fibrous scar tissue membrane bridging the defect in the bone. The critical size for holes in the calvarium in adult rats is 8 mm. i.e. holes 8 mm or of large diameter will not be closed by bone tissue.

In rats a paramedial skin incision is made from the nasofrontal area to the external occipital protuberance. The skin and the underlying tissues, including most of the temporal muscle on either side, are detached. A specially manufactured trephine is used to create a 8 mm hole in the skull bilaterally. Extreme care is taken to avoid damage to the meninges and the brain.

On the right side a chitosan membrane with ionically bonded heparin prepared as in Example 9 s placed on the dura, multiple bone fragments positioned on the membrane and an additional identical membrane positioned on the skull. Thereafter, on the left side a non-heparinized chitosan membrane prepared as in Example 5 is positioned in the same way with spacing bone fragments. Thereafter, the galea and the skin are closed.

After 3 weeks the rats are anaesthetized and the scull examined. More osteoid and new bone tissue could be demonstrated to cover the defect on the right side as compared to the left side. There is in addition less prominent inflammatory reaction at the heparinized chitosan membranes.

Example 12

Preparation of chitosan beads covered with dextransulphate or heparin or chondroitin-4-sulphate Aqueous solutions of chitosan (2% w/v, 18% acetylated) is added drop by drop with a syringe to a solution of dextransulphate or heparin or chondroitin-4-sulphate (0.1% w /v) in tripolyphosphate buffer. The resulting beads are recovered on a glass filter and rinsed with water (1 L) and dried at 30 ° C0 over night.

Example 13

Osteogenic activity of chitosan beads as assessed by bone formation after subperiostal deposition on the skull Positioning of a compound to be tested for osteogenic activity under the periostium of the skull is a well established method.

Beads made of chitosan and heparin, chitosan coated with dextran sulphate and chitosan coated with chondroitin-4-sulphate, pared as described in Example 12, are positioned subperiostally on the frontal bone of adult rats. One such bead is positioned on either side. Bone formation is assessed after 3 weeks.

Chitosan-heparin beads are osteogenic as revealed by the formation of osteoid and bone tissue on the frontal bone. The chrondritin sulphate coated chitosan beads and the dextran sulphate coated ones do also show osteogenic activity. Inflammatory cells could be recognized to variable, usually low, extent as well. These experiments demonstrate that chitosan combined with certain polysaccharides exert osteogenic activity.

Even better stimulation of healing quality can probably be achieved by a combination of this invention with growth factors.

Experiments in vitro with aFGF labelled with iodine 125 (acidic Fibroblast Growth Factor, Bachem Calif.) show a significantly higher specific binding of growth factor to a heparinized screw as compared to a non-heparinized screw. Even if the invention is not restricted to any particular theory it seems likely that endogeneous growth factors are enriched at the interface between implant and surrounding bone when the screw is provided with a coating of chitosan-heparin, thus resulting in stimulated bone regeneration.

The invention is not limited to the embodiments described but is applicable to all forms of implant intended for integration into hard tissue, particularly bone tissue. Thus, the invention is applicable within all areas, for example odontology, orthopedics, neurosurgery, hand surgery and plastic and reconstructive surgery. Also with regard to dental applications the invention is quite useful.

We claim:

1. A process to stimulate regeneration of hard tissue at a hard tissue site, comprising the step of applying onto the hard tissue site an amount active for stimulation of an agent comprising a chitosan to which at least one other polysaccharide is immobilized which is selected from the group consisting of heparin, heparan sulfate, chondroitin sulfates and dextran sulfate.

2. The process according to claim 1, wherein the hard tissue site comprises a cavity in a hard tissue structure, the cavity having a boundary surface for anchorage of an implant having a boundary surface.

3. The process according to claim 2, wherein the agent is applied to the boundary surface of the implant to stimulate the regeneration of the surrounding hard tissue structure.

4. The process according to claim 3, further comprising applying the agent to the implant by dipping the implant in a solution of chitosan and at least one other polysaccharide whereupon the implant is located in a cavity in the hard tissue structure.

5. A process for osseointegration of an implant in a bone comprising the steps of:
 (a) providing an implant;
 (b) providing a bone cavity having a boundary surface for surrounding the implant; and
 (c) applying an osteogenic agent to the cavity or the implant or both;
  the agent essentially consisting of an unmodified a chitosan and at least one other polysaccharide immobilized thereto, the other polysaccharide being selected from the group consisting of heparin, heparin sulfate, chondroitin sulfate, and dextran sulfate, so as to stimulate bone regeneration at an interface between the implant and the surrounding bone.

6. The process according to claim 1 or 5, wherein said agent is in the form of a powder.

7. The process according to claim 1 or 5, wherein said agent is in the form of a gel.

8. The process according to claim 1 or 5, wherein the other polysaccharide is heparin or heparin sulfate.

9. The process according to claim 1 or 5, wherein the other polysaccharide is immobilized to the chitosan by means of ionic bonds.

10. The process according to claim 1 or 5, wherein the other polysaccharide is immobilized to the chitosan by means of covalent bonds.

11. The process according to claim 1 or 5, wherein the agent is in the form of a solution.

12. The process according to claim 1 or 5, wherein the agent is in the form of beads.

13. The process according to claim 1 or 5, wherein the chitosan has a degree of N-acetylation of less than about 90%.

14. The process according to claim 1 or 5, wherein the chitosan has a degree of N-acetylation of less than about 50%.

15. The process according to claim 1 or 5, wherein the chitosan has a degree of N-acetylation of less than about 25%.

16. An adapted to be anchored in a cavity of a hard tissue structure, wherein the implant is coated with an agent for stimulating regeneration of hard tissue at the boundary interface between the implant and the hard tissue cavity, the agent comprising chitosan and a polysaccharide immobilized thereto the polysaccharide being selected from the group consisting of heparin, heparan sulfate, chondroitin sulfates and dextran sulfate.

17. The implant according to claim 16, wherein the implant comprises titanium.

* * * * *

UNITED STATES PATENT AND TRADEMARK OFFICE
CERTIFICATE OF CORRECTION

PATENT NO. : 5,894,070
DATED : April 13, 1999
INVENTOR(S) : Hansson et al.

It is certified that error appears in the above-identified patent and that said Letters Patent is hereby corrected as shown below:

Claim 5, col. 7, line 42, delete "a", and at col. 8, lines 2-3, delete "heparin sulfate" and substitute therefor -- heparan sulfate --.

Claim 16, col. 8, line 32, insert -- implant -- between "An" and "adapted".

Signed and Sealed this

Eleventh Day of January, 2000

Attest:

Attesting Officer

Q. TODD DICKINSON
Acting Commissioner of Patents and Trademarks